United States Patent [19]
Horrobin et al.

[11] Patent Number: 5,116,624
[45] Date of Patent: May 26, 1992

[54] EFA COMPOSITIONS AND THERAPY

[75] Inventors: David F. Horrobin, Guildford, England; Frank Corrigan, Argyll, Scotland

[73] Assignee: Efamol Holdings plc, Surrey, United Kingdom

[21] Appl. No.: 638,998

[22] Filed: Jan. 9, 1991

[30] Foreign Application Priority Data

Jan. 18, 1990 [GB] United Kingdom ................. 9001121

[51] Int. Cl.$^5$ ..................... A61K 31/20; A61K 33/04
[52] U.S. Cl. ..................................... 424/702; 514/560
[58] Field of Search .......................... 514/560; 424/702

[56] References Cited

PUBLICATIONS

Chem. Abst. 111-6411 S-1989.

*Primary Examiner*—S. J. Friedman
*Attorney, Agent, or Firm*—Nixon & Vanderhye

[57] ABSTRACT

A pharmaceutical composition of GLA or DGLA and bioavailable selenium, optionally also with an 18:4 or higher n-3 EFA and/or bioavailable zinc.

5 Claims, No Drawings

EFA COMPOSITIONS AND THERAPY

FIELD OF INVENTION

The invention relates to pharmaceutical compositions of essential fatty acids (EFAs) and treatment of disease therewith.

BACKGROUND

Dementia and depression are common psychiatric disorders. They frequently occur together in the same patient.

While there are many drugs which treat depression, not all patients respond. Moreover, most of these drugs have important side effects which limit their usefulness. There is therefore a need for new, safe treatments for depression.

Dementia can be caused by a variety of underlying disorders, the most important being Alzheimer's disease, multi-infarct dementia, and infections with certain viruses or virus-like agents. The cause of Alzheimer's disease is unknown but there is loss of nerve cells in key areas of the brain. In multi-infarct dementia, cell death follows reduced oxygen and blood flow as a consequence of multiple blockages of small arteries. There are no known satisfactory treatments for dementia of any type.

FATTY ACIDS

The pathways of conversion of the main series of polyunsaturated fatty acids in the body are as in Table 1 below:

TABLE 1

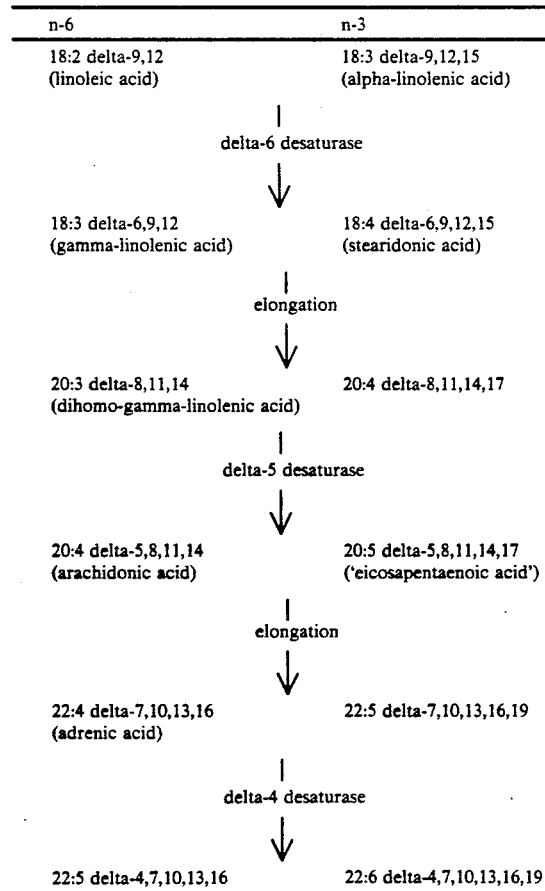

| n-6 | n-3 |
|---|---|
| 18:2 delta-9,12 (linoleic acid) | 18:3 delta-9,12,15 (alpha-linolenic acid) |
| delta-6 desaturase | |
| 18:3 delta-6,9,12 (gamma-linolenic acid) | 18:4 delta-6,9,12,15 (stearidonic acid) |
| elongation | |
| 20:3 delta-8,11,14 (dihomo-gamma-linolenic acid) | 20:4 delta-8,11,14,17 |
| delta-5 desaturase | |
| 20:4 delta-5,8,11,14 (arachidonic acid) | 20:5 delta-5,8,11,14,17 ('eicosapentaenoic acid') |
| elongation | |
| 22:4 delta-7,10,13,16 (adrenic acid) | 22:5 delta-7,10,13,16,19 |
| delta-4 desaturase | |
| 22:5 delta-4,7,10,13,16 | 22:6 delta-4,7,10,13,16,19 |

TABLE 1-continued

| n-6 | n-3 |
|---|---|
| | ('docosahexaenoic acid') |

The above pathways are not normally reversible nor, in man, are n-3 and n-6 series acids interconvertible.

The acids, which in nature are of the all-cis configuration, are systematically named as derivatives of the corresponding octadecanoic, eicosanoic or docosanoic acids, e.g. delta-9,12-octadecadienoic acid or delta-4,7,10,13,16,19-docosahexaenoic acid, but numerical designations such as, correspondingly, 18:2 n-6 or 22:6 n-3 are convenient. Initials, for example, EPA for the 20:5 n-3 acid (eicosapentaenoic acid) or DHA for the 22:6 n-3 acid (docosahexaenoic acid), are also used but do not serve when n-3 and n-6 acids of the same chain length and degree of unsaturation exist as for example with the 22:5 acids. Trivial names in more or less common use in the n-6 series are as shown. Of the n-3 series only 18:3 n-3 has a commonly used trivial name, alpha-linolenic acid, though the name stearidonic acid is coming into use for the 18:4 n-3 acid and the names eicosapentaenoic acid and docosahexanenoic acid as such are also used. The alpha isomer of linolenic acid was characterised earlier than gamma-linolenic acid and reference in the literature simply to linolenic acid, especially in the earlier literature, is to the alpha-acid.

EXPERIMENTAL

The cell membranes of nerve cells in the brain are rich in EFAs derived as above from dietary linoleic acid (LA) and alpha-linolenic acid (ALA). Unlike other tissues of the body, the brain contains very little linoleic acid and alpha-linolenic acid: almost all its EFAs are in the form of derivatives of the dietary acids arising from initial 6-desaturation, and are required for normal membrane structure and normal function. Since the 6-desaturation of linoleic acid and alpha-linolenic acid is a slow, rate-limiting step which can be interfered with by many factors, administration of these acids is not a good way to elevate brain EFA levels. It is better for such a purpose to administer acids such as gamma-linolenic acid (GLA) and dihomo-gamma-linolenic acid (DGLA) of the n-6 family, and stearidonic acid (18:4 n-3), eicosapentaenoic acid (EPA) and docosa-hexaenoic acid (DHA) of the n-3 family. These acids are often referred to as "6-desaturated" EFAs, a loose but convenient term for the acids arising in the body by the pathways detailed above and involving the initial 6-desaturation of the dietary acid.

Since the cell membranes of the brain are so rich in 6-desaturated EFAs it seemed worthwhile, in initial work that has led to this invention, to test their effects in dementia and depression. We therefore performed a study in thirty patients with dementia of the Alzheimer type (twenty three female, seven male, average age 78 years). They were examined by several standard tests, including the anomalous sentences repetition test (ASRT), the coloured progressive matrices test (CPMT), the graded naming test (GNT), the digit copying test (DCT) and the Hamilton Depression Rating Scale (HDRS). The first four tests are widely used to measure dementia, while the Hamilton scale is the most widely used measure of depression.

Half the patients were given gamma-linolenic acid (GLA) in the form of evening primrose oil (6 g/day containing about 500 mg of GLA), equivalent to giving DGLA as conversion is very rapid in the human body. These patients were also given zinc sulphate (200 mg/day) and sodium selenite (2 mg/day) each mg containing about 457 microg elemental selenium). The other half of the patients were given placebo corresponding to the GLA, zinc and selenium.

The significance of zinc is that it is known to potentiate some actions of GLA (EP-A-0,003,407, U.S. Pat. No. 4,273,763). However, in a previous study in long stay psychiatric patients, GLA alone or in combination with zinc failed to improve depression and had only a small effect on memory although it did improve the schizophrenic features of psychosis (Horrobin and Vaddadi, unpublished results). Zinc alone therefore does not synergise with GLA in treatment of dementia or depression. The inventors then decided to add selenium to the treatment regime in the study, the rationale being that EFAs are highly susceptible to oxidation and can be easily destroyed. Selenium can inhibit the oxidation of EFAs and also, as a component of the enzyme glutathione peroxidase, help to eliminate any harmful peroxides which may be formed by EFA oxidation. There are therefore strong reasons for combining GLA and DGLA and selenium. The GLA and/or DGLA will raise the levels of the appropriate EFAs at important sites in the body: the selenium will inhibit the oxidation of these important compounds and will also help to remove any oxidation products which happen to be formed. This inter-action between GLA/DGLA and selenium is in no way dependent on the presence of zinc and will occur entirely independently of zinc. Zinc may improve the responses to GLA and selenium even further by increasing the availability of the GLA or DGLA.

In the trials, the patients were randomly allocated to the active and placebo groups and the trial was conducted on a double-blind basis. The patients were treated for twenty weeks and the tests were performed before treatment started and at the end of treatment.

After twenty weeks there were no significant changes in the placebo group, whose scores remained close to baseline values. The results in the active group are shown in Table 2. It appears that selenium can greatly enhance the effect of GLA on both the dementia and the depression, improvements that are remarkable in a disease that is currently regarded as intractable. Moreover, the effects were achieved without producing any important side effects. In the table it should be noted that changes in scores are given, for the patients treated with GLA and zinc plus selenium. The change from baseline to the end of the trial was assessed statistically by the Wilcoxon nonparametric test. For the ASRT, CPMT, GNT and DCT, an *increase* in score represents an improvement. For the HDRS a *decrease* in score represents an improvement.

TABLE 2

| TEST | BASELINE | END OF TRIAL | SIGNIFICANCE, $2P<$ |
|---|---|---|---|
| ASRT | $72.6 \pm 28.8$ | $87.5 \pm 36.7$ | 0.005 |
| CPMT | $12.2 \pm 6.7$ | $15.8 \pm 8.6$ | 0.005 |
| GNT | $7.2 \pm 5.2$ | $9.8 \pm 5.4$ | 0.005 |
| DCT | $61.2 \pm 20.0$ | $69.7 \pm 22.2$ | 0.01 |
| HDRS | $4.4 \pm 3.1$ | $1.9 \pm 1.8$ | 0.005 |

SUMMARY OF INVENTION

From the above, the invention in its various aspects lies in:

1. As such or when for use in therapy, particularly of dementia and/or depression, a pharmaceutical composition of GLA or DGLA with a form of selenium which is bioavailable, optionally also with an 18:4 or higher n-3 EFA (notably 18:4, 20:5, 22:5, 22:6) and/or bioavailable zinc.

2. A method of treating or preventing dementia with a combination of GLA or DGLA and bioavailable selenium, optionally with such n-3 EFA and/or zinc.

3. A method of treating or preventing depression with a combination of GLA or DGLA and bioavailable selenium, optionally with such n-3 EFA and/or zinc.

4. A method of preparation of a medicament for use in curative or prophylactic therapy against dementia, depression or both, characterised in that said medicament comprises GLA or DGLA for use with bioavailable selenium in the course of said therapy, or bioavailable selenium for use with GLA or DGLA in the course of said therapy, or both said GLA and DGLA and said selenium for use in the course of said therapy, said medicament optionally in each case comprising also an n-3 EFA and/or zinc as set out at 1. above.

DOSES AND FORMATS

The GLA or DGLA may be used at 1 mg to 20 g/day, preferably 50 mg to 4 g and very preferably 200 mg to 2 g. Like amounts of n-3 EFAs, where present, may be used. GLA can be synthesised but it is usually derived from natural oils such as those of the evening primrose, blackcurrant or borage, or the storage oils of various fungi. GLA and other EFAs can be administered in any biologically assimilable form, such as the free acid, salt, ester, amide, phospholipid or natural or synthetic tri-glycerides. It can be administered in any convenient way, e.g. orally, parenterally, topically or rectally, as can the compositions as a whole. DGLA as such is not readily available, but fungal sources are known and chemical synthesis is possible; amounts for administration are as for GLA.

The selenium may be used at 1 to 10,000 microg per day, (elemental selenium basis) preferably 50 to 2000 microg/day, very preferably 200 to 1000 microg/day. The selenium too can be administered in any convenient way, i.e. orally, parenterally, rectally or topically in any biologically assimilable form. Possible forms include sodium selenite, selenious acid, selenomethionine and selenium yeast (yeast grown in a bioavailable selenium containing environment).

The GLA and selenium, and the zinc and n-3 EFAs when used, may be incorporated in the same formulation for ease of administration or may be provided separately or in sub-combinations for co-administration. In particular the EFAs may sometimes be conveniently given as a general dietary supplement, and possibly the zinc as well if used, the selenium being administered under more direct medical supervision.

Bioavailable forms of zinc, for example zinc gluconate and zinc sulphate, are well known and amounts may for example be 1 to 800 mg/day, preferably 2.5 to 800 mg/day, more preferably 5 to 80 mg/day (elemental zinc basis).

DERIVATIVES OF EFAs

As indicated above, the acids may be used as such or as pharmaceutically acceptable and physiologically equivalent derivatives as, for example, detailed later herein for GLA and DGLA, and reference to any of the acids is to be taken as including reference to the acids when in the form of such derivatives. Equivalence is demonstrated by entry into the pathway quoted herein, as evidenced by effects corresponding to those of the acids themselves or their natural glyceride esters. Thus, indirect identification of useful derivatives is by their having the valuable effect in the body of the acid itself, but conversion can be shown directly by gas chromatographic analysis of concentrations in blood, body fat, or other tissue by standard techniques, for example those of Pelick et al, page 23, "Analysis of Lipids and Lipoproteins" Ed Perkins, American Oil Chemists Society, Champaign, Ill., U.S.A.

In outline the method is suitably that plasma samples (1 ml) are extracted with chloroform:methanol (2:1). The extract is filtered through sodium sulphate, evaporated to dryness, and taken up in 0.5 ml chloroform:methanol. The lipid fractions are separated by thin layer chromatography or silica gel plates. The phospholipid fraction, taken to reflect essential fatty acid contents most sensitively, is methylated using boron trifluoride-methanol. The resulting methyl esters of the fatty acids are separated and measured using a Hewlett-Packard 5880 gas chromatograph with a six foot column packed with 10% silar on chromosorb WAW 106/230. The carrier gas is helium (30 ml/min). Oven temperature is programmed to rise from 165° C. to 190° C. at 2° C./min. Detector temperature is 220° C. and injector temperature 200° C. Retention times and peak areas are automatically computed by Hewlett-Packard Level 4 integrator. Peaks are identified by comparison with standard fatty acid methyl esters.

DIETARY COMPOSITIONS

The invention is chiefly described in terms of methods of treatment and pharmaceutical compositions, but it will be understood that the gamma-linolenic and other EFAs, being in the nature of dietary supplements, can be incorporated in a dietary margarine or other foodstuff and such are to be understood as within the term pharmaceutical composition when for the purposes set out.

FORMS AND SOURCES OF GAMMA-LINOLENIC AND OTHER ACIDS

Convenient physiologically equivalent derivatives of GLA and DGLA for use according to the invention as with the other essential fatty acids, include salts, amides, esters including glyceride esters and alkyl (e g. $C_1$ to $C_4$) esters, and phospholipids.

If desired, pharmaceutical compositions may be produced for use in the invention by associating the natural or synthetic acids, as such or as derivatives, with an acceptable pharmaceutical vehicle. It is, however, at present convenient to provide at least the GLA in the form of an available oil having a high GLA content, hence reference to "oil" herein.

One source of oils currently available is the seed of evening primrose species such as *Oenothera biennis L.* and *Oenothera lamarckiana,* the oil extract therefrom containing about 8% GLA and about 72% linoleic acid in the form of their glycerides, together with other glycerides (percentages based on total fatty acids). Other sources of GLA are borage species such as *Borago officinalis* which, though current yield per acre is low, provide a richer source than Oenothera oil. Oils from the seeds of members of the Ribes family are also often rich in GLA. Recent studies on fungi which can be cultivated by fermentation promise a fungal oil source.

The oil is extracted from the seed by one of the conventional methods of extraction such as cold pressure, screw pressure after partially cooking the seed, or solvent extraction.

Fractionation of a typical sample of this oil in the form of methyl esters shows the relative proportions:

| | |
|---|---|
| Palmitate | 6.15 |
| Stearate | 1.6 |
| Oleate | 10.15 |
| Linoleate | 72.6 |
| Gamma-linolenate | 8.9 |

The seed oil extracts referred to above can be used as such or can, for example, if desired, be fractionated to yield an oily composition containing the triglycerides of gamma-linolenic and linoleic acids as the main fatty acid components, the gamma-linolenic acid content being, if desired, a major proportion. Seed oil extracts appear to have a stabilising effect upon DGLA if present.

SOURCES OF OTHER ACIDS

DGLA can be prepared by chemical synthesis or by fungal fermentation.

The n-3 acids are available from marine oils, particularly the 20:5 n-3 and 22:6 n-3 acids, and recently from microbial fermentation.

The acids can be isolated from these sources by, for example, saponification under mild non-oxidising conditions followed by preparative gas liquid chromatography. Synthesis of the acids is difficult but not impossible and provides another source.

PHARMACEUTICAL PRESENTATION

As mentioned briefly above, the compositions are conveniently in a form suitable for oral, rectal or parenteral administration in a suitable pharmaceutical vehicle, as discussed in detail, for example, in Williams British Patent Specification No. 1,082,624, to which reference may be made, and in any case very well known generally for any particular kind of preparation. Thus, for example, tablets, capsules, ingestible liquid or powder preparations can be prepared as required, and topical preparations also when the gamma-linolenic acid or other acids are absorbed through the skin. Injectable solutions of hydrolysed Oenothera oil may be prepared using albumin to solubilise the free acid.

Advantageously, a preservative is incorporated into the preparation. Alpha-tocopherol in concentration of about 0.1% by weight has been found suitable for the purpose, and there are other stabilisers such as ascorbyl palmitate or stearate, all well known in the field.

It will be understood that the absolute quantity of active materials present in any dosage unit should not exceed that appropriate to the rate and manner of administration to be employed but on the other hand should also desirably be adequate to allow the desired rate of administration to be achieved by a small number of doses. The rate of administration will moreover depend on the precise pharmacological action desired.

EXAMPLES

Dementia and depression, occurring separately or together, are treated with the following:

1. Soft gelatin capsules containing 500 mg evening primrose oil (EPO, 40 to 45 mg GLA) and 0.1 mg sodium selenite, 12 caps/day.
2. Soft gelatin capsules containing 500 mg EPO, 0.1 mg sodium selenite, 100 mg fish oil (containing 20 mg of EPA and 8 mg of DHA), and 10 mg of zinc gluconate, 10 caps/day.
3. Hard gelatin capsules containing 200 mg of purified GLA or DGLA and seleno-methionine or selenium yeast containing 100 microg elemental selenium, 6 caps/day.
4. A syrup containing in each 5 ml (teaspoonful) 250 mg GLA and 200 microg selenium in the form of seleno-methionine, 6 tsp/day.
5. A foam whip containing in each 5 ml 300 mg of DGLA and 150 microg selenium in the form of selenium yeast, taken correspondingly to Example 4 at 6×5 ml/day.
6. A fluid for parenteral administeration containing in each 5 ml 500 mg of GHLA and 500 microg of elemental selenium in the form of sodium selenite, 5 ml given daily.
7. A topical formulation containing 100 mg/ml GLA and 100 microg/ml selenium in the form of seleno-methionine, 10 ml applied daily.
8. Soft gelatin capsules containing 200 mg DGLA, 50 mg DHA, 200 microg sodium selenite and 30 mg zinc gluconate, 6 cap/day.
9. Soft gelatin capsules containing 400 mg GLA, 50 mg stearidonic acid, 30 mg zinc sulphate and 200 microg selenium as selenium yeast, 4 caps/day.

We claim:

1. A method of treating dementia in a person having same comprising administering to said person an effective amount of a composition comprising, per unit dose, 1 mg to 20 g of GLA, DGLA or both together with 1 to 10,000 micrograms of bioavailable selenium.
2. A method of treating depression in a person having same comprising administering to said person an effective amount of a composition comprising, per unit dose, 1 mg to 20 g of GLA, DGLA or both together with 1 to 10,000 micrograms of bioavailable selenium.
3. The method of claim 1 or 2 in which the composition also contains from 1 to 800 mg of bioavailable zinc.
4. The method of claim 1 or 2 in which the composition also contains from 1 mg to 20 g of an 18:4 or higher n-3 essential fatty acid.
5. The method of claim 3 in which the composition contains both bioavailable zinc and from 1 mg to 20 g of an 18:4 or higher n-3 essential fatty acid.

* * * * *